US00RE35230E

United States Patent [19]

van Eikeren

[11] E Patent Number: Re. 35,230

[45] Reissued Date of Patent: May 7, 1996

[54] ENANTIOMERIC ENRICHMENT OF CYANOHYDRINS

[75] Inventor: Paul van Eikeren, Carlisle, Mass.

[73] Assignee: Bend Research, Inc., Bend, Oreg.

[21] Appl. No.: 192,867

[22] Filed: Feb. 7, 1994

Related U.S. Patent Documents

Reissue of:

[64] Patent No.: 5,241,087
Issued: Aug. 31, 1993
Appl. No.: 848,023
Filed: Mar. 9, 1992

[51] Int. Cl.[6] ..... C07C 253/32; C07C 253/34; C12P 13/00; C12P 41/00

[52] U.S. Cl. ..... 435/280; 435/128; 549/422; 549/491; 554/113; 558/354; 558/410; 558/423; 558/430; 558/431; 558/432; 558/433; 558/434; 558/451; 546/330

[58] Field of Search ..... 558/354, 410, 558/423, 451, 430, 431, 432, 433, 434; 435/128, 280; 549/442, 491

[56] References Cited

U.S. PATENT DOCUMENTS

| | | | |
|---|---|---|---|
| 4,560,515 | 12/1985 | Stoutamire et al. | 558/354 |
| 4,656,303 | 4/1987 | Kurono et al. | 558/451 X |
| 4,900,667 | 2/1990 | Arena | 558/410 X |
| 4,966,726 | 10/1990 | Scherowsky et al. | 558/428 X |
| 5,008,192 | 4/1991 | Neidermeyer et al. | 435/280 X |
| 5,122,462 | 6/1992 | Miethe et al. | 435/280 X |
| 5,241,087 | 8/1993 | Eikeren | 549/442 |
| 5,256,569 | 10/1993 | Yoshida et al. | 435/280 |
| 5,296,373 | 3/1994 | Endo et al. | 435/280 |
| 5,346,816 | 9/1994 | Griengl et al. | 435/280 X |

OTHER PUBLICATIONS

Hackh's Chemical Dictionary, 4th Ed., Grant–Editor (1969), p. 410.

*Primary Examiner*—Joseph Paul Brust
*Attorney, Agent, or Firm*—Chernoff, Vilhauer, McClung & Stenzel

[57] ABSTRACT

A method of enantiomerically enriching chiral cyanohydrins is disclosed that involves selective cleavage of the unwanted enantiomer into its cleavage products HCN and the corresponding aldehyde or ketone by use of an enantioselective dehydrocyanation catalyst, coupled with simultaneous removal of at least one of the dehydrocyanation products.

19 Claims, 5 Drawing Sheets

ENANTIOMERIC ENRICHMENT OF CYANOHYDRINS

Matter enclosed in heavy brackets [ ] appears in the original patent but forms no part of this reissue specification; matter printed in italics indicates the additions made by reissue.

The government has a nonexclusive, nontransferable, royalty-free license to practice this invention under Contract No. ISI-8960705 awarded by the National Science Foundation.

*This application is a Reissue of 07/848,023 filed Mar. 9, 1992, now U.S. Pat. No. 5,241,087.*

BACKGROUND OF THE INVENTION

Cyanohydrins of the structure

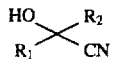

where $R_1$ and $R_2$ are selected from hydrogen and substituted or unsubstituted alkyl or aryl, are important starting materials and intermediates in the preparation of a large number of biologically active compounds. See for example, 99 Ang. Chemie 491 (1987). When $R_1$ and $R_2$ are different, such cyanohydrins are chiral and so exist as (R)- and (S)-enantiomers, generally in equal proportions, known as racemic mixtures. When cyanohydrin derivatives that contain chiral centers are used to prepare biologically active substances, it is often highly desirable that they be in an enantiomerically-enriched or pure form, as opposed to in a racemic mixture, so as to improve biological specificity and reduce side effects.

Cyanohydrins are generally prepared by hydrocyanation, which involves adding hydrogen cyanide to aldehydes or ketones. Several methods used to synthesize enantiomerically-enriched cyanohydrins use chiral hydrocyanation catalysts to catalyze enantioselective addition of hydrogen cyanide to aldehydes and ketones according to the general reaction

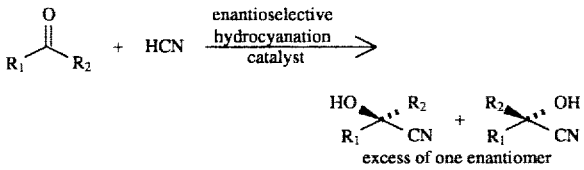

where, for example, the products contain a greater percentage ("enantiomeric excess") of one enantiomer relative to the other enantiomer. Such syntheses are known as asymmetric cyanohydrin syntheses. Known enantioselective hydrocyanation catalysts useful in such asymmetric cyanohydrin syntheses include (R)- and (S)-oxynitrilases (see 46 Tet. 979 (1990) for (R)-oxynitrilases and 31 Tet. Lett. 1249 (1990) for (S)-oxynitrilases); cyclic peptides (see for example U.S. Pat. No. 4,569,793 for use of cyclo-(R)-phenylalanyl-(R)-histidine and cyclo-(S)-phenylalanyl-(S)-histidine dipeptides); cyclodextrins (see 39 Aust. J. Chem. 1135 (1986) for use of crystalline β-cyclodextrin complexes); tartaric acid complexes (see European Patent Application No. 0 271 *868* for use of titanium complexes); and rhenium π-aldehyde complexes (see for example, 30 Tet. Lett. 3931 (1989)). However, these asymmetric cyanohydrin syntheses frequently produce products of inadequate enantiomeric excess because of the competing non-enantioselective base-catalyzed hydrocyanation reaction. Consequently, there is a need for alternative methods to produce chiral cyanohydrins in enantiomerically enriched or pure form.

An alternative to using an enantioselective hydrocyanation catalyst to prepare chiral cyanohydrins is enantioselective dehydrocyanation, that is, the use of an enantioselective catalyst to effect the enrichment of a mixture of chiral cyanohydrins by preferentially converting one enantiomer in the mixture into hydrogen cyanide and the corresponding aldehyde or ketone. Such a reaction may be depicted by the equation below.

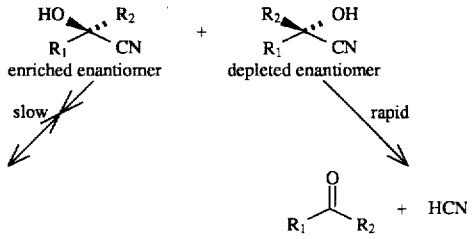

In principle, such a reaction can transform a mixture of cyanohydrin enantiomers into a mixture of cyanohydrins enriched in one enantiomer, the corresponding aldehyde or ketone, and hydrogen cyanide.

There are a few reports that describe enantioselective catalysts that preferentially convert one enantiomer in a mixture of cyanohydrins into hydrogen cyanide and the corresponding aldehyde or ketone. Gerstner et al., in 353 Z. Physiol. Chem. 271 (1972), reported that the enzyme D-oxynitrilase (D-alphaoxynitrile lyase, EC 4.1.2.10) catalyzes the reversible addition of hydrogen cyanide to a variety of aldehydes to form D-cyanohydrins. Mao et al., in 6 Phytochemistry 473 (1967), reported that the oxynitrilase enzyme from sorghum appears to be specific for the dehydrocyanation of p-hydroxybenzaldehyde cyanohydrin.

U.S. Pat. No. 3,649,457 discloses the enantioselective dehydrocyanation of D,L-mandelonitrile (benzaldehyde cyanohydrin) to enrich the same in L-mandelonitrile with an (R)-oxynitrilase catalyst that is attached to a soluble polymer to maintain it in the reaction solution, yet cause it to be rejected by an ultrafiltration membrane that allows all reactants and reaction products to pass. There is no teaching of simultaneous trapping or removal of either the aldehyde or HCN, nor of the advantages which flow therefrom.

Dehydrocyanation reactions are characterized by unfavorable dehydrocyanation equilibria; the equilibrium of a typical dehydrocyanation reaction strongly favors formation of the cyanohydrin. For example, given the dehydrocyanation equilibrium constant for benzaldehyde cyanohydrin of 5 mM, a 1M solution of benzaldehyde cyanohydrin exposed to a dehydrocyanation catalyst will undergo only about 7% conversion to benzaldehyde and hydrogen cyanide when allowed to reach equilibrium. Enantioselective dehydrocyanation represents a kinetic resolution, and such a resolution is optimally carried out under conditions where the equilibrium strongly favors formation of the products. Because the equilibrium of a dehydrocyanation reaction strongly favors reactants, such a reaction would not appear to lend itself for use in a kinetic resolution.

SUMMARY OF THE INVENTION

The present invention comprises a method of enantiomerically enriching a mixture of cyanohydrins by biasing the reaction so that the unwanted enantiomer undergoes a dehydrocyanation reaction to hydrogen cyanide and the corresponding aldehyde or ketone. In its broadest sense, the present invention involves the use of enantioselective hydrocyanation catalysts to preferentially convert one enantiomer in a mixture of chiral cyanohydrins into hydrogen cyanide and the corresponding aldehyde or ketone (enantioselective dehydrocyanation) while simultaneously trapping one or both of the dehydrocyanation products. The generalized reaction scheme is shown below.

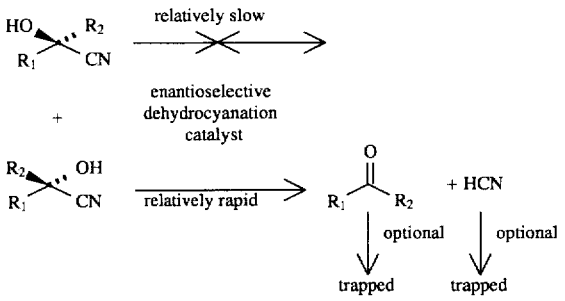

Because kinetic resolutions provide enantiomeric enrichment by allowing the unwanted enantiomer to undergo reaction, enantiomeric enrichments approaching 100% are attainable by appropriate selection of the extent of conversion. Because the product of the dehydrocyanation reaction is the corresponding aldehyde or ketone, it can be separated from cyanohydrin by simple extraction and the isolated aldehyde or ketone can be reconverted to racemic cyanohydrin for reuse.

DETAILED DESCRIPTION OF THE INVENTIONS

TERMS & CONVENTIONS

Figure 1:
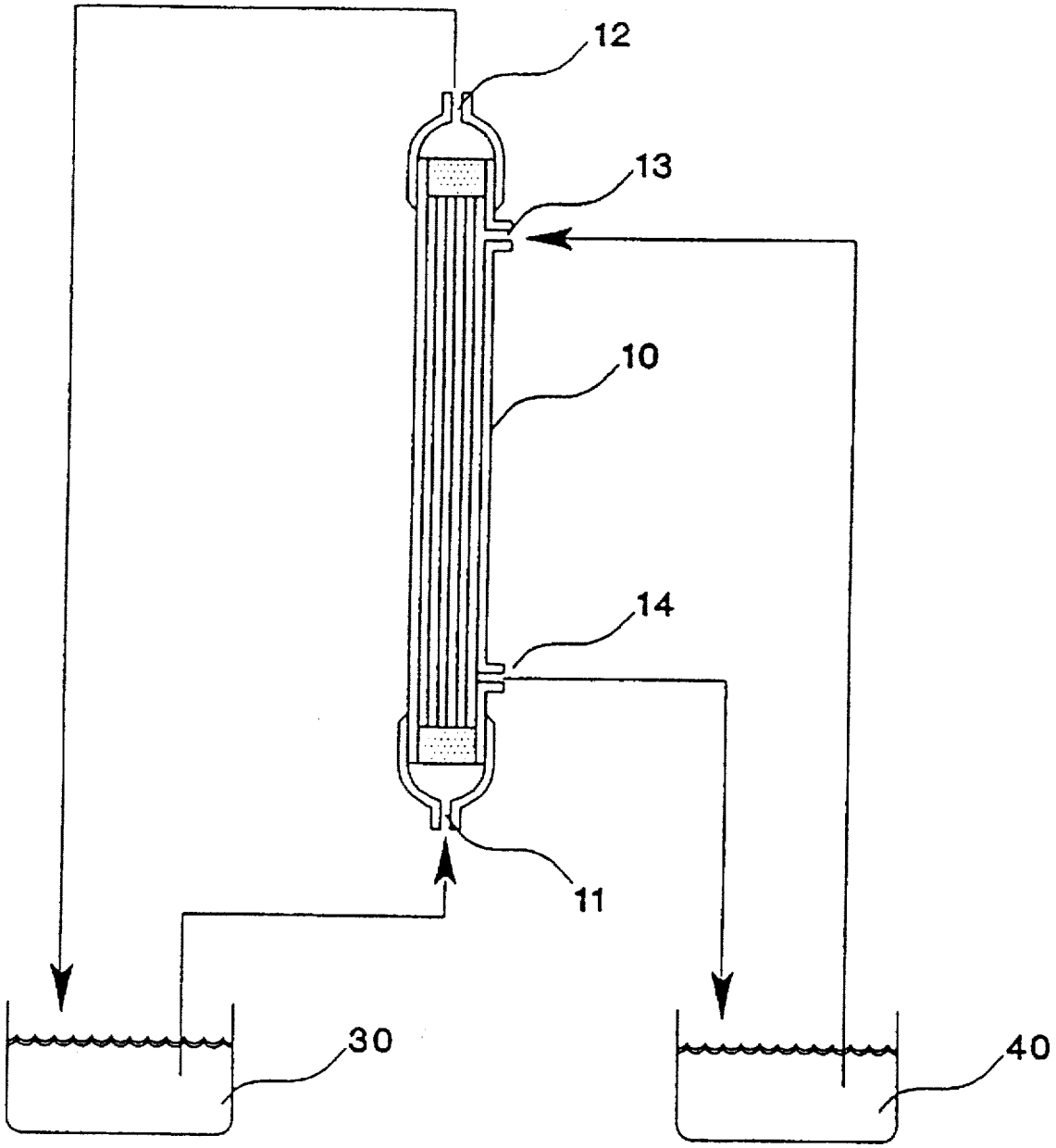
FIG. 1 is a schematic of an exemplary system for the removal and trapping of hydrogen cyanide.

Assignment of R- and S- designations to chiral formulae are made according to the Cahn-Ingold-Prelog method and depend upon preassigned values for the substituents $R_1$ and $R_2$ in the general cyanohydrin structure set forth above, according to the Sequence Rule.

The reaction involved in the present invention can be depicted as

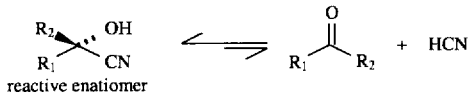

wherein broadly speaking each $R_1$ and $R_2$, taken independently, is an alkyl or aryl group which is unsubstituted or substituted with one or more catalytically non-inhibiting groups, and $R_1$ is different from $R_2$. The reaction is characterized by a dehydrocyanation equilibrium constant, defined as $$K_{dehydcn} = \frac{[R_1COR_2][HCN]}{[R_1COHCNR_2]}$$

where the terms in brackets correspond to the equilibrium concentrations. The value of $K_{dehydcn}$ for most cyanohydrins is substantially less than 1M, reflecting that the equilibrium strongly favors the reverse reaction comprising the addition of hydrogen cyanide to the corresponding aldehyde or ketone (hydrocyanation).

The term "hydrocyanation catalyst" means any organic, organometallic, inorganic, or protein-based substance which exhibits the property of catalyzing the hydrocyanation reaction.

The term "dehydrocyanation catalyst" is meant any organic, organometallic, inorganic, or protein-based substance which exhibits the property of catalyzing the dehydrocyanation reaction.

The term "enantioselective hydrocyanation catalyst" means a catalyst that is preferentially active with respect to one of a mixture of said chiral cyanohydrins, i.e., that enhances the rate of hydrocyanation to form one enantiomer relative to the rate of hydrocyanation to form the other enantiomer.

The term "enantioselective dehydrocyanation catalyst" means a catalyst that is preferentially active with respect to one of a mixture of chiral cyanohydrins, i.e., that enhances the rate of dehydrocyanation of one enantiomer relative to the rate of dehydrocyanation of the other enantiomer.

The term "trapping" refers to physical and chemical processes which reduce the concentration of HCN or aldehyde or ketone in the dehydrocyanation reaction. Trapping effectively permits the hydrocyanation reaction, the thermodynamics of which for many cyanohydrins are strongly in favor of cyanohydrin production, to be operated in reverse, as a dehydrocyanation reaction.

The term "enantiomeric enrichment" refers to the increase in the amount of one enantiomer as compared to the other. Enantiomeric enrichment may be effected by a decrease in the amount of one chiral form as compared to the other. A convenient method of expressing enantiomeric enrichment uses the concept of enantiomeric excess ("ee"), expressed by $$\%\ ee = \frac{[E1 - E2]}{[E1 + E2]} \times 100$$

wherein E1 is the amount of the first chiral form of the cyanohydrin and E2 is amount of the second chiral form of the same cyanohydrin. Thus, if the initial ratio of the two chiral forms E1 and E2 is 50:50, as in a racemic mixture, and an enantiomeric enrichment is achieved that is sufficient to produce a final E1 to E2 ratio of 75:25, the ee with respect to the first chiral form would be 50%, calculated as $$\%\ ee = \frac{[75 - 25]}{[75 + 25]} \times 100 = 50$$

The term "catalytically non-inhibiting groups" refers to optional substituents on the substituents $R_1$ and/or $R_2$ that do not significantly affect or compete with the action of the dehydrocyanation catalyst when the chiral cyanohydrin carrying that group is present in practical concentrations.

The term "adjuvants" refers to optional substances that are added to the reaction medium to enhance the effectiveness of the dehydrocyanation catalyst.

According to the present invention, there is provided a process for the enantiomeric enrichment of a mixture of two enantiomeric chiral cyanohydrins of the structures IA and IB

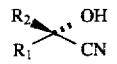

IA

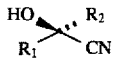

IB comprising (a) bringing the mixture of chiral cyanohydrins into contact with an enantioselective dehydrocyanation catalyst until one of said chiral cyanohydrins is converted in a dehydrocyanation reaction to an aldehyde or ketone of the structure II

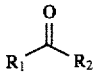

II and (b) simultaneously trapping at least one of the dehydrocyanation reaction products so as to shift the equilibrium of the dehydrocyanation reaction in the direction of dehydrocyanation.

The invention is based on the discovery that trapping dehydrocyanation reaction products during the course of contacting known enantioselective hydrocyanation catalysts with a mixture of cyanohydrin enantiomers significantly improves both yield and enantiomeric enrichment.

CYANOHYDRIN STARTING MATERIALS

The chiral cyanohydrins IA and IB employed in the process of the present invention have structural constraints. $R_1$ and $R_2$ must render the molecule chiral, that is, $R_1$ must necessarily be different from $R_2$ in structure or chirality or $R_1$ and $R_2$ taken together, form a chiral group. Generally, taken independently, $R_1$ and $R_2$ may be substituted or unsubstituted alkyl, cycloalkyl, or aryl groups. By "alkyl" is meant both straight and branched-chain alkyl groups. By "aryl" is meant phenyl, phenylalkyl and naphthyl groups. Classes of examples of such $R_1$ and $R_2$ substituents include straight and branched alkyl groups containing from 1 to 24 carbon atoms, cycloalkyl groups containing from 3 to 12 carbon atoms, a phenyl group, a naphthyl group, and straight and branched phenylalkyl groups containing from 7 to 24 carbon atoms. More specific examples include the groups methyl, ethyl, n-propyl, i-propyl, n-butyl, i-butyl, s-butyl, phenyl, benzyl, phenethyl, 1-phenethyl, 2-phenylpropyl, etc. Preferably, $R_1$ is as just described and $R_2$ is hydrogen.

Since the catalytic reaction in the present invention involves the cyanohydrin group and its associated carbon atom, each $R_1$ and $R_2$ group optionally may be substituted with one or more groups, provided that they are catalytically non-inhibiting groups as defined above. This can readily be determined by a simple inhibition assay. Even when inhibition is detected, it can be minimized by conducting the reaction with a lower concentration of reactant or by maintaining the reactant at a lower steady state concentration by feeding reactant to the reaction solution. Suitable substituents include halo such as chloro, fluoro, bromo and iodo, hydroxy, lower alkyl, lower alkoxy, lower alkylthio, cycloalkyl, carbamoyl, mono- and di-(lower alkyl) substituted carbamoyl, trifuoromethyl, phenyl, nitro, alkylsulfonyl, arylsulfonyl, alkylcarboxamide, and arylcarboxamido.

When $R_1$ and $R_2$ taken together form a chiral group, suitable examples comprise alkyl chains that form a ring containing from 3 to 18 carbons. Specific examples of this class of substituents include propane-1,2-diyl, butane-1,3-diyl, 1-propene-1,3-diyl, pentane-1,4-diyl, 2-methyl-butane-1,4-diyl, 1-butene-1,4-diyl, hexane-1,5-diyl, 2-methyl-pentane-1,5-diyl, 1-pentane-1,5-diyl, and 2-pentane-1,5-diyl.

Cyanohydrins for which the present invention may be used for enantiomeric enrichment include the cyanohydrins resulting from the addition of hydrogen cyanide to aromatic aldehydes, to alkyl-substituted aldehydes, and to asymmetrically substituted ketones. Examples of aromatic aldehydes include benzaldehyde, p-methoxybenzaldehyde, 5-methylfurfuraldehyde, piperonaldehyde, 3-m-phenoxybenzaldehyde, 2-furfuraldehyde, p-methylbenzaldehyde, p-chlorobenzaldehyde, p-hydroxybenzaldehyde, m-chlorobenzaldehyde, m-bromobenzaldehyde, m-hydroxybenzaldehyde, m-methoxybenzaldehyde, m-methylbenzaldehyde, o-methoxybenzaldehyde, p-nitrobenzaldehyde, m-nitrobenzaldehyde, p-cyanobenzaldehyde, 2-napthaldehyde, 6-methoxy-2-napthaldehyde, pyridine-3-carboxaldehyde, and p-ethylbenzaldehyde. Examples of alkyl-substituted aldehydes include acetaldehyde, propionaldehyde, butyraldehyde, crotonaldehyde, 2,2,5,5-tetrahydrobenzaldehyde, cinnamaldehyde, trimethylacetaldehyde, phenylacetaldehyde, 3-methylmercaptopropionaldehyde, acrolein, isobutyraldehyde, isovaleraldehyde, cyclohexanecarboxaidehyde, pentanal, hexanal, methyl 9-oxo-nonanoate, and (E)-3,7-dimethyl-2,6-octadienal. Examples of asymmetrically substituted ketones include methyl ethyl ketone, methyl isopropyl ketone, methyl t-butyl ketone, 2-methylcyclohexanone, 2-methyl-cyclobutanone, 2-methyl-cyclopentanone, 3-methyl-cyclopentanone, methyl cyclohexyl ketone, trifluoroacetophenone, and t-butyl phenyl ketone.

An especially preferred cyanohydrin starting material is m-phenoxybenzaldehyde cyanohydrin, as the (S)-enantiomer thereof is present in several commercially important pyrethroid insecticides. See 33 J. Acr. Food Chem. 508 (1985). A preferred starting racemic mixture for the process of the present invention comprises racemic chiral cyanohydrin, although previously enantiomerically-enriched mixtures will serve as well. Table 1 contains a summary of cyanohydrins suitable as starting materials, some of which are shown in the Examples herein.

TABLE 1

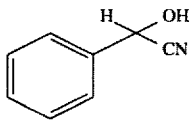

Benzaldehyde cyanohydrin

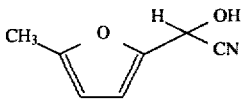

5-Methylfurfural cyanohydrin

TABLE 1-continued

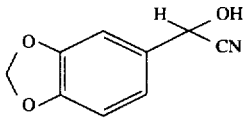

Piperonal cyanohydrin

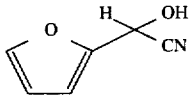

Furfural cyanohydrin

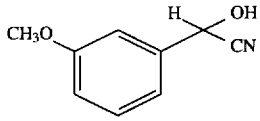

m-Anisaldehyde cyanohydrin

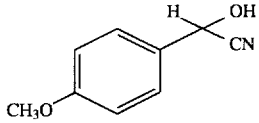

p-Anisaldehyde cyanohydrin

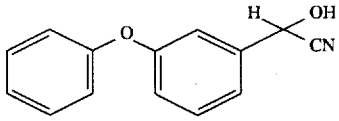

m-Phenoxybenzaldehyde cyanohydrin

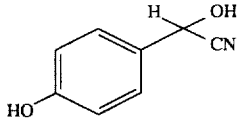

p-Hydroxybenzaldehyde cyanohydrin

CATALYSTS

Suitable dehydrocyanation catalysts useful in the present invention comprises all known enantioselective hydrocyanation catalysts, including those mentioned in the Background of the Invention herein. Two especially preferred class of catalysts comprise the oxynitrilase enzymes. Two oxynitrilases which are particularly useful in the present invention, (R)-oxynitrilase (EC 4.1.2.10) and (S)-oxynitrilase (EC 4.1.2.11), have been isolated and characterized. A second preferred class of catalysts are the cyclic peptides, including cyclo[(S)-phenylalanyl-(S)-histidyl], cyclo[(R)-phenylalanyl-(R)-histidyl], cyclo[(S)-alanyl-(S)-histidyl], cyclo[(R)-alanyl-(R)-histidyl], cyclo[(S)-histidyl-(S)-histidyl], cyclo[(R)-histidyl-(R)-histidyl], cyclo[(S)-valinyl-(S)-histidyl], cyclo[(R)-valinyl-(R)-histidyl], cyclo[(S)-prolyl-(S)-histidyl], and cyclo[(R)-prolyl-(R)-histidyl].

Dehydrocyanation catalysts used in the present invention may be in free form or immobilized on suitable supports. For example, oxynitrilases may be used as cell-free extracts or immobilized on a suitable support matrix such as Celite (See Wehtje et al., 36 Biotech. Bioengin. 39 (1990)) or Avicell (See Effenberger et al., 26 Angew. Chem. Int. Ed. Engl. 458 (1987)). Immobilized oxnitrilases are particularly useful since once prepared, one need merely feed the mixture of chiral cyanohydrins dissolved in a suitable solvent over the immobilized enzyme in order to effect the desired enrichment, and then isolate the unreacted cyanohydrin and separate the formed aldehyde/ketone as described in further detail below.

REACTION CONDITIONS

The dehydrocyanation reaction is preferably conducted in a liquid phase that may be an organic liquid, an aqueous-based liquid or a mixture of miscible or immiscible liquids, including emulsions and two-phase mixtures. Selection of the liquid phase is dictated primarily by the requirements of the trapping method used, but any liquid may be used as long as the cyanohydrin exhibits some solubility in the phase in which the dehydrocyanation catalyst is present. The concentration of cyanohydrin is not at all critical, as any convenient concentration will do which affords a solution of sufficiently low viscosity to ensure adequate contact with the dehydrocyanation catalyst and with the secondary liquid phase (if present). In cases where the catalyst and all adjuvants are dissolved in one or more liquid phases, the cyanohydrin may be introduced as a solid. The concentration of dehydrocyanation catalyst is selected such that the initial rate of the catalyzed dehydrocyanation reaction is at least ten-fold higher than the initial rate of racemization due to the background hydrocyanation/dehydrocyanation reaction. The performance of the dehydrocyanation catalyst, especially enzymes, is maintained optimally by controlling the pH of the aqueous phase with buffers, removing any enzyme inhibitors present, and including adjuvants that minimize the inactivation of the catalyst.

When the dehydrocyanation reaction is carried out in aqueous solution, selection of solution pH is an important factor governing the apparent enantio-selectivity of the catalyst. The dehydrocyanation is preferably carried out at low pH to minimize the non-selective hydroxide-ion-catalyzed hydrocyanation reaction which leads to the formation of racemic cyanohydrin and has the effect of reducing the apparent enantioselectivity of the catalyst. However, use of very low pH values result in low catalyst productivities because the activity of many catalysts, such as (R)-oxynitrilase enzyme, decreases markedly at low pH. Consequently, the dehydrocyanation reaction carried out by (R)-oxynitrilase catalysts are preferably carried out in the range of pH 3.5 to 5.5. Optimum pH ranges for other catalysts are readily ascertainable by measuring the activity and the apparent selectivity as a function of pH and then choosing the best compromise between productivity and selectivity.

When the undesired chiral form of the cyanohydrin is converted to hydrogen cyanide and the corresponding aldehyde or ketone and the desired chiral form is not, the dehydrocyanation reaction is preferably allowed to proceed to an extent that results in a ratio of at least 3:1 of the desired chiral form to the undesired chiral form, representing an ee of at least 50%. The mixture of cyanohydrins, enriched in the desired form, can be readily isolated by conventional techniques. For example, a partial separation can be effected by acidifying the solution to stabilize the unreacted cyanohydrin, followed by extraction of the same with a solvent such as hexane, diethylether, or dichloromethane. Contaminating aldehyde or ketone present in the organic extract can be removed by washing the organic extract with aqueous sodium bisulfite solution. Recovered aldehyde or ketone can be reused by converting it to racemic cyanohydrin using conventional techniques.

TRAPPING

Trapping the dehydrocyanation reaction products while the dehydrocyanation reaction is taking place keeps the concentrations of the dehydrocyanation reaction products below their equilibrium values and thus maintains a thermodynamic driving force to direct the dehydrocyanation reaction to completion. Trapping improves both the yield and the enantiomeric excess of the unreacted cyanohydrin. Virtually any method of removing and trapping either HCN or the aldehyde/ketone dehydrocyanation products, or both, is suitable in the present invention. Exemplary methods include gas-liquid extraction, liquid-liquid extraction, membrane-based separation, chemical conversion of the dehydrocyanation products, or any combination thereof.

More specific exemplary methods of removing and trapping include: (1) conducting the dehydrocyanation reaction in a gas-liquid two phase system wherein the gas phase serves as an extraction agent for the removal of at least one dehydrocyanation reaction product; (2) conducting the dehydrocyanation reaction in a liquid two-phase system wherein one of the phases functions as an extraction agent that is selective for removal of at least one of the dehydrocyanation reaction products; (3) conducting the dehydrocyanation reaction in a membrane system wherein one or both dehydrocyanation products are removed by selective passage through one or more membranes; (4) conducting the dehydrocyanation reaction in the presence of reagents that selectively react and thereby trap one or both of the dehydrocyanation reaction products; and (5) any combination of (1), (2), (3) or (4).

Trapping by gas-liquid extraction is a useful method to continuously remove the dehydrocyanation reaction product hydrogen cyanide. The method is also useful to remove aldehyde or ketone dehydrocyanation reaction product. Removing aldehyde or ketone dehydrocyanation product is preferred when such a product exhibits a vapor pressure above the liquid that is larger than the vapor pressure of the cyanohydrin above the liquid. A conventional and useful measure of the vapor pressure above the liquid is the Henry's Law constant. Almost any gas that is inert with respect to the reactants, catalyst, solvent and adjuvants present in the dehydrocyanation reaction mixture is useful. Especially preferred gas-phase extractants are nitrogen, helium, neon, argon, methane, ethane, propane, and combinations of such gases with each other or air. Trapping by gas-liquid extraction can be carried out by any suitable method used to contact gases with liquids; preferred methods include sweeping the gas over the surface of the liquid and bubbling the gas through the liquid. Trapping is preferably conducted by supplying a volume of gas that is large relative to the volume of the liquid and in the form of a continuous stream, and may be carried out at atmospheric, subatmospheric, and superatmospheric pressures of the gas.

Trapping by liquid-liquid extraction is an alternate suitable method to continuously remove dehydrocyanation reaction products. The method is especially useful to remove aldehyde or ketone dehydrocyanation reaction product when such a product exhibits low solubility in the catalyst-containing phase and exhibits higher partitioning into the non-catalyst-containing phase than does the cyanohydrin undergoing hydrocyanation. A conventional and useful measure of the degree of partitioning of a given species into a liquid is the partition coefficient. Almost any liquid that is inert with respect to the reactants, catalyst, solvent and adjuvants present in the dehydrocyanation reaction mixture, that is immiscible with the liquid phase in which the dehydrocyanation is carried out, and that dissolves the dehydrocyanation reaction products, is useful in the present invention.

When the enantiomeric mixture of cyanohydrins undergoing enrichment is a liquid and is immiscible with the catalyst-containing solvent and forms a separate organic phase, this organic phase can itself serve as the extracting agent to trap the dehydrocyanation reaction products. Enantiomeric enrichment of such immiscible enantiomeric mixtures of cyanohydrins is especially effective when the solubility of the aldehyde reaction product in the catalyst-containing solvent is low and is lower than the solubility of the mixture of cyanohydrins in the catalyst-containing solvent. For example, trapping by liquid-liquid extraction during the enrichment of m-phenoxybenzaldehyde cyanohydrin is effective because m-phenoxybenzaldehyde is an organic liquid that is immiscible with water and is only soluble in water to the extent of approximately 2 mM. Consequently, m-phenoxybenzaldehyde cyanohydrin itself can be used to effectively extract its dehydrocyanation product, m-phenoxybenzaldehyde, which is only soluble in water to the extent of approximately 0.3 mM. Other examples of cyanohydrins that form an immiscible organic phase and can be enriched by the above method include furfural cyanohydrin, m-anisaldehyde cyanohydrin, and piperonal cyanohydrin.

Other suitable extractants include but are not limited to the following: hydrocarbon solvents (including hexane, heptane, octane, squalane), aromatic solvents (including benzene, toluene, xylene, alkyl-substituted biphenyls ["Shell-Solve 325" by Shell Oil Corporation], diisopropyl biphenyl), ether solvents (diethyl ether, diisopropyl ether, methyl-tertiary-butyl ether, n-butyl ether), and chlorinated hydrocarbons (dichloromethane, chloroform, 1,2-dichlooethane). Trapping by liquid-liquid extraction can be carried out by any suitable method used to contact two-immiscible liquids with the aim of enhancing mass-transfer between liquids including but not limited to stirred tanks, countercurrent extraction columns, and countercurrent centrifugal extractors.

Trapping by membrane-based processes provides yet another alternative method to continuously remove and trap dehydrocyanation reaction products. The method is particularly useful for removing and trapping hydrogen cyanide produced in the dehydrocyanation reaction. A preferred membrane separation process for the removal of hydrogen cyanide present in aqueous or aqueous/organic solutions comprises supported-gas membranes, but other membrane processes can be useful. Supported-gas membranes consist of a thin film of gas, generally air, supported and stabilized in the pores of microporous membranes fabricated from hydrophobic polymers. Supported-gas membranes are highly selective and efficient for the transport of hydrogen cyanide (See Kenfield et al., 10 Environ. Sci. Tech. 1151 (1988) and dehydrocyanation products that exhibit large Henry's Law constants.

Supported-gas membranes for use in the present invention are membranes capable of transporting the dehydrocyanation reaction products by a solution diffusion mechanism. The solution diffusion transport of dehydrocyanation products through such membranes occurs in three stages. Focusing on the selective transport of a single dehydrocyanation reaction product (solute), in the first stage the transported solute enters the membrane by dissolving in the surface of the membrane to a concentration dictated by its concentration in solution and its intrinsic distribution coefficient. For supported-gas membranes, distribution coefficients are expressed as Henry's Law constants, which relate the vapor pressure of the solute above an aqueous solution to the concentration of the solute in the aqueous solution. Supported-gas membranes are especially suitable for trapping methods where the dehydrocyanation reaction products exhibit high Henry's Law constant values relative to such values for the cyanohydrins. In the second stage, the transported solute diffuses through the membrane to the other surface at a velocity dictated by the diffusion constant in the membrane material and the magnitude and direction of the concentration gradient across the membrane. In the third stage, the transported solute exits the membrane by partitioning into the solution on the far side of the membrane.

An especially preferred class of membranes useful in trapping the reaction products in the present invention is supported-gas membranes. Broadly speaking, supported-gas membranes comprise a thin film of immobilized gas stabilized in the pores of a porous matrix. A preferred gas is air and preferred porous matrices are microporous membranes fabricated from hydrophobic polymers such as polytetrafuoroethylene, polydifluoroethylene, polyethylene, and polypropylene. Commercially available membranes that can function as supported-gas membranes include the Celgard Series of polypropylene flat sheet and hollow fiber membranes (Celanese, Charlotte, N.C.); Goretex polytetrafluoroethylene flat sheet membranes (W. L. Gore & Assoc.); 60TW polypropylene hollow fiber membranes (Mitsubishi Rayon America, N.Y.); and Microdyn polypropylene hollow fiber membranes (Enka AG, Germany).

Figure 2:
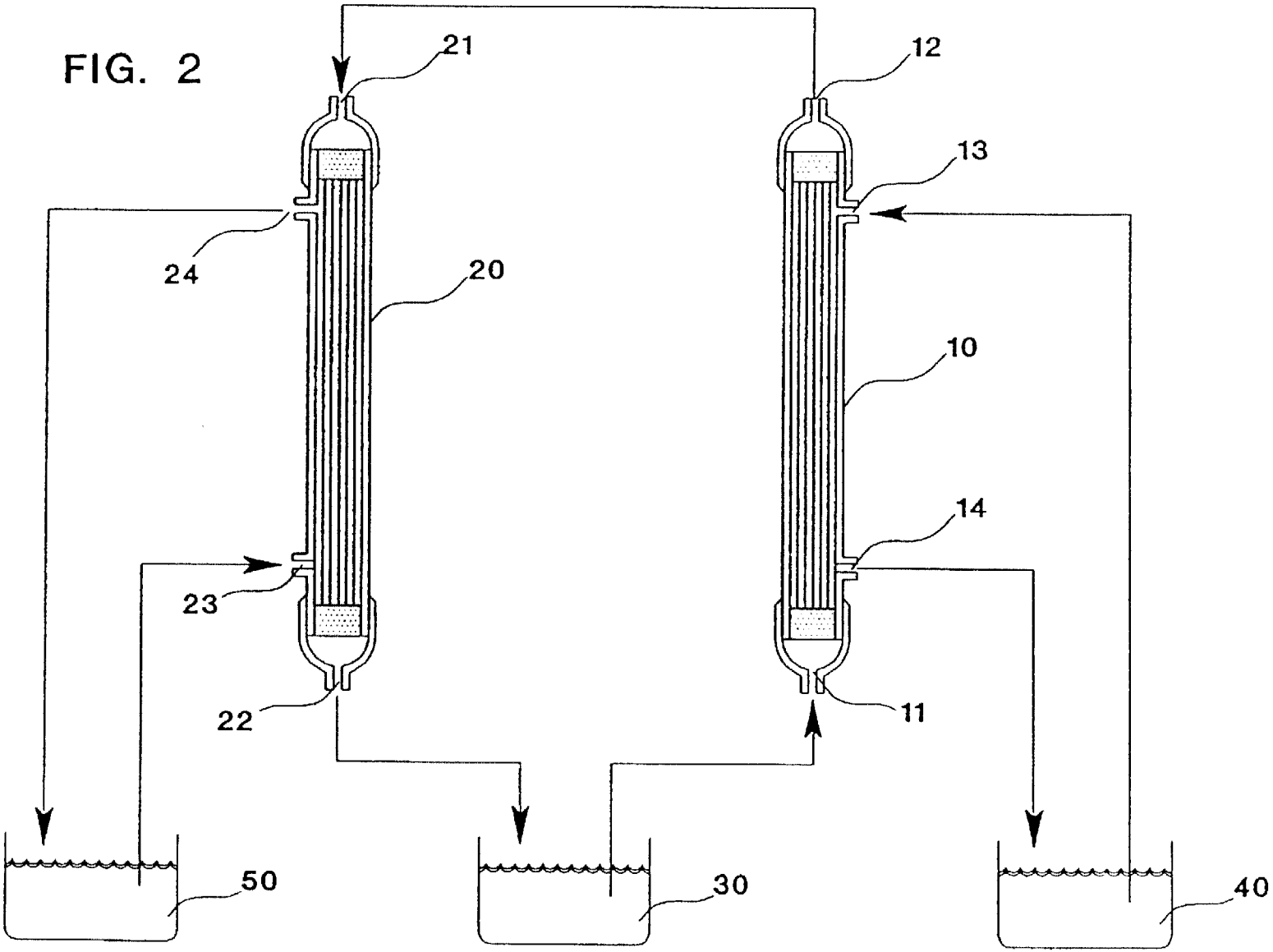
FIG. 2 is a schematic of an exemplary system for the removal and trapping of aldehydes and ketones.

Turning to FIGS. 1 and 2, wherein like numerals designate the same elements, an exemplary system for the removal and trapping of hydrogen cyanide is shown schematically in FIG. 1, comprising a supported-gas membrane module 10 containing a bundle of microporous polypropylene hollow fibers (8200 $cm^2$) having an I.D. of 400 microns, a wall thickness of 29 microns, and a porosity of 40%; a feed reservoir 30 of an aqueous reaction solution of the enantioselective catalyst, cyanohydrin, dehydrocyanation products, and optional adjuvants; and a strip reservoir 40 containing an aqueous alkaline solution of, for example, 0.1M NaOH.

In operation, the aqueous reaction solution in reservoir 30 is circulated through the lumens of the hollow fibers of the module 10 into feed port 11 and out exit port 12 back to feed reservoir 30. At the same time, the alkaline strip solution from strip reservoir 40 is circulated on the outside or "shell" side of the hollow fibers, entering the module 10 at entry port 13 and leaving through exit port 14, and back to strip reservoir 40. During operation, hydrogen cyanide and high Henry's law constant aldehydes or ketones present in the aqueous solution of reservoir 30 partition between the aqueous solution and the gas in the supported gas membrane. Transport across the membrane to the far interface occurs by diffusion at a rate and extent dictated by the concentration gradient. At the far interface, hydrogen cyanide and aldehydes or ketones having a high Henry's Law constant partition between the gas in the supported-gas membrane and the aqueous strip solution. Partitioning into the strip solution is enhanced by diluting the transported hydrogen cyanide and aldehydes or ketones into relatively large volumes of aqueous solution or by allowing them to undergo a chemical reaction that transforms them into species with low Henry's Law constants. For example, including sodium hydroxide in the strip solution converts hydrogen cyanide, a species with a high Henry's Law constant, into cyanide ion, which has a relatively low Henry's Law constant. Similarly, the inclusion of sodium bisulfite in the strip solution converts the dehydrocyanation reaction product benzaldehyde, which has a high Henry's Law constant, into benzaldehyde bisulfite adduct, a species having relatively low Henry's Law constant.

The system of FIG. 1 was used to ascertain the degree of permeability of cyanohydrins and their corresponding dehydrocyanation reaction products HCN and aldehyde to ascertain the selectivity of the membrane-based removing and trapping scheme. Results showed that, for benzaldehyde cyanohydrin and its dehydrocyanation products HCN and benzaldehyde, the average permeabilities of both dehydrocyanation products was approximately equal and roughly 700 times the permeability of benzaldehyde cyanohydrin, demonstrating a high selectivity for the removal and trapping of the dehydrocyanation products by such a system.

Another exemplary system that uses both the membrane-based process described above to remove and trap hydrogen cyanide and an additional membrane-based process to remove aldehydes and ketones having low Henry's Law constants is shown schematically in FIG. 2. The system comprises two membrane modules: one is the same supported-gas membrane module 10 shown in FIG. 1 with an aqueous alkaline strip solution circulated on the shell side of the hollow fiber membranes from strip reservoir 40; the second is a membrane contactor module 20 with an organic strip solution circulated on the shell side of the hollow fiber membranes from a second strip reservoir 50. Membrane contactor modules suitable for the present invention include regenerated cellulose and polyacrylonitrile fiber bundles embedded in polycarbonate or stainless-steel shells with polyurethane or epoxy potting compound. An exemplary membrane contactor module 20 comprises a bundle of regenerated cellulose hollow fibers (427 $cm^2$; Baxter Travenol) with an I.D. of 200 microns, and a wall thickness of 11 microns.

During operation, feed reservoir 30 is charged with an aqueous solution containing enantioselective catalyst, adjuvants, and cyanohydrin. Membrane contactor 20 is used in conjunction with supported-gas membrane module 10 by circulating the feed solution from exit port 12 of module 10 to entry port 21 of membrane contactor 20, through the lumens of the hollow fiber membranes and back to feed reservoir 30 via exit port 22. Recirculation flow rates suitable for the present invention range from 100 to 500 ml/min. Hydrogen cyanide produced during the dehydrocyanation reaction is removed from the aqueous solution by the supported-gas membrane module as described in connection with FIG. 1. Aldehyde/ketone dehydrocyanation product is removed by membrane-contactor module 20 by diffusive transport across the membrane and preferential partitioning into the organic strip liquid.

For cyanohydrins that are sparingly soluble in water, strip reservoir 50 and the associated membrane contactor module 20 serve a secondary function. Enrichment of racemic cyanohydrin takes place by dissolving it in the organic solvent in strip reservoir 50. During operation, racemic cyanohydrin in the organic solvent may be circulated as the feed to the shell side of the hollow fibers of membrane contactor 20 via feed port 23, exiting via exit port 24, which results in equilibration of racemic cyanohydrin between the organic solvent and the aqueous solution circulating the lumens of the hollow fiber membranes of module 20, which results in a transfer of racemic cyanohydrins back to feed reservoir 30, thereby feeding racemic cyanohydrin to the dehydrocyanation reaction.

The continuous removal of dehydrocyanation products from organic (as opposed to aqueous) solutions can also be carried out by membrane-based methods. In these cases, the supported-gas membranes are coated on the side facing the organic solution with a thin polymer film coating which minimizes the intrusion of organic liquid into the pores but allows the permeation of hydrogen cyanide by diffusion. Suitable polymer coatings include but are not limited to rubbery polymers such as dimethylsiloxane, polyisobutylene, and polyacetylene, and water-swollen gel polymers such as polyacrylic acid and polyvinyl alcohol.

Converting the dehydrocyanation reaction products to substances which cannot undergo the hydrocyanation reaction is another useful trapping method in the present invention. Especially preferred are the use of reagents and/or catalysts that effect the reaction of hydrogen cyanide. An exemplary hydrogen cyanide removal reaction is reaction of hydrogen cyanide with reagents to form the corresponding cyanohydrins. Such reagents include aldehydes, ketones, aldoses and ketoses. Exemplary aldehydes are formaldehyde, alkyl aldehydes such as acetaldehyde, n-butyraldehyde, and isobutyraldehyde, and substituted aromatic aldehydes such as m-chlorobenzaldehyde, m-nitrobenzaldehyde, o-chlorobenzaldehyde, and o-nitrobenzaldehyde. Exemplary ketones are cyclic ketones such as cyclopropanone, cyclobutanone, cyclohexanone, and substituted cyclohexanones. Exemplary aldoses are glyceraldehyde, erythrose, threose, ribose, arabinose, xylose, lyxose, allose, altrose, glucose, mannose, gulose, idose, galactose and tallose. Exemplary ketoses are dihydroxyacetone, ribulose, xylulose, psicose, fructose, sorbose, and tagatose. Selection of reagent is guided by the principle that preferred reagents should exhibit smaller dehydrocyanation constants than dehydrocyanation equilibrium constant of the cyanohydrin undergoing enrichment, although reagents that exhibit larger cyanohydrin dehydrocyanation equilibrium constants will also work by using them at higher concentrations.

Other reagents suitable for removing hydrogen cyanide include n-alkyl pyridinium salts, alkene epoxides, and alkyl halides. In addition, one can employ catalysts that hydrolyze hydrogen cyanide into formamide and formic acid. Exemplary catalysts include a class of enzymes called cyanidases, which are described by Ingvorsen et al. in European Patent Application No. 0 282 351. Hydrogen cyanide removal reactions are preferably carried out under acidic or substantially neutral conditions to minimize the base-catalyzed dehydrocyanation of the cyanohydrin undergoing enrichment, which would otherwise reduce the yield of chiral cyanohydrin in the enantiomeric enrichment process and could result in racemization of the cyanohydrin undergoing enrichment.

Another method [of] *to* achieve trapping involves including reagents and/or catalysts that effect the reaction of the aldehyde or ketone dehydrocyanation products. Exemplary aldehyde or ketone removal reactions include reaction with bisulfite to form bisulfite adducts; reaction with amines or diamines to form Schiff bases; reaction with hydroxylamine to form hydroxamates; reaction with hydrazine or substituted hydrazines to form hydrazones; and reaction of aldehydes with oxidants such as molecular oxygen, peroxide, perchlorate, perbromate, periodate, chlorate, bromate, iodate, chlorine, bromine, and iodide to form carboxylic acids. These reagents can be used dissolved in solution or in an immobilized form.

CATALYST ACTIVITY

Catalyst activity may be expressed as units/mg for solid catalysts and units/ml for dissolved catalysts. A unit of catalyst activity is conveniently defined as the dehydrocyanation of one micromole of cyanohydrin per minute. For purposes of uniformity, benzaldehyde cyanohydrin is used as the standard cyanohydrin. For example, one unit of (R)-oxynitrilase activity corresponds to the amount of enzyme that converts benzaldehyde cyanohydrin to benzaldehyde and hydrogen cyanide at a rate of one micromole per minute.

The following standardized assay was utilized to measure the activity of oxynitrilase set forth in the Examples which follow. A solution of enzyme was prepared in 0.1M (pH 5.5) citrate buffer. A 3-ml sample of enzyme solution was combined with 30 microliters of 0.21 M benzaldehyde cyanohydrin and the rate of increase in absorbance at 250 nm recorded. Then, the same procedure was followed with a 3-ml sample of 0.1M (pH 5.5) citrate buffer to obtain the background, non-enzymatic, reaction. The activity in units/ml was calculated by subtracting the slope of the non-enzymatic reaction from the slope of the enzymatic reaction and converting the absorbance change with time to concentration change with time using a molar extinction coefficient of 13,200 $M^{-1}cm^{-1}$.

MONITORING THE REACTION

The progress of the dehydrocyanation reaction was monitored by one of two methods. In the first method, reaction aliquots were removed, acidified with sulfuric acid to stabilize the cyanohydrin, and extracted with chloroform. The organic extract was analyzed by liquid chromatography on a C-18 reverse phase column (25 cm×2 mm) employing isocratic elution using a mixture of methanol and 0.05M aqueous trifluoroacetic acid (60/40; vol/vol) with detection at 250 nm. In the second method, the cyanohydrin was extracted with chloroform as described above, then treated with bis(trimethylsilyl)acetamide to convert the cyanohydrin to the trimethylsilyl derivative and analyzed by capillary gas chromatography on an HP-1 dimethylpolysiloxane column (25 m×0.2 mm) with flame ionization detection.

MEASUREMENT OF EE

The enantiomeric excess of cyanohydrins was measured by one of two methods. In the first method, the specific rotation was compared to the specific rotation of samples of known enantiomeric excess. In the second method, samples of cyanohydrin were allowed to react with (−)-alpha-(trifluoromethylphenyl)methoxyacetyl chloride according to the method reported by Mosher et al. in 34 J. Org. Chem. 2543 (1969) and the resulting diastereomers were separated by capillary gas chromatography on an HP-1 dimethylpolysiloxane column (25 m×0.2 mm) with flame ionization detection.

PARTITION COEFFICIENTS

Partition coefficient studies of cyanohydrins and their corresponding aldehydes in organic solvents and aqueous buffer solutions were made and confirmed that the aldehydes partition much more strongly into the organic phase than do the corresponding cyanohydrins.

ACTIVITY OF (R)-OXYNITRILASE TOWARD CYANOHYDRINS

Relative rates of dehydrocyanation of different cyanohydrins subjected to the action of the soluble catalyst (R)-oxynitrilase were determined from initial rate studies. A solution of (R)-oxynitrilase was combined with a 0.21 mM solution of cyanohydrin and the rate of increase of absorbance at the wavelength corresponding to the absorption maxima was monitored as described above in connection with the measurement of catalyst activity. The measured activity was calculated using the appropriate extinction coefficient for the corresponding aldehyde. The results, summarized in Table 2, demonstrate that (R)-oxynitrilase catalyzes dehydrocyanation of a range of cyanohydrin structures and that it is unexpectedly more effective with several unnatural substrates than with its natural substrate, benzeldehyde cyanohydrin.

TABLE 2

| Cyanohydrin Substrate | Relative Rate |
|---|---|
| 5-Methylfurfural cyanohydrin | 2.8 |
| Furfural cyanohydrin | 2.5 |
| Piperonal cyanohydrin | 2.1 |
| Benzaldehyde cyanohydrin | 1.0 |
| Crotonaldehyde cyanohydrin | 0.90 |
| P-Tolualdehyde cyanohydrin | 0.45 |
| m-Anisaldehyde cyanohydrin | 0.19 |
| p-Anisaldehyde cyanohydrin | 0.17 |
| p-Ethylbenzaldehyde cyanohydrin | 0.13 |
| Cinnamaldehyde cyanohydrin | 0.05 |

EXAMPLE 1

Figure 3:
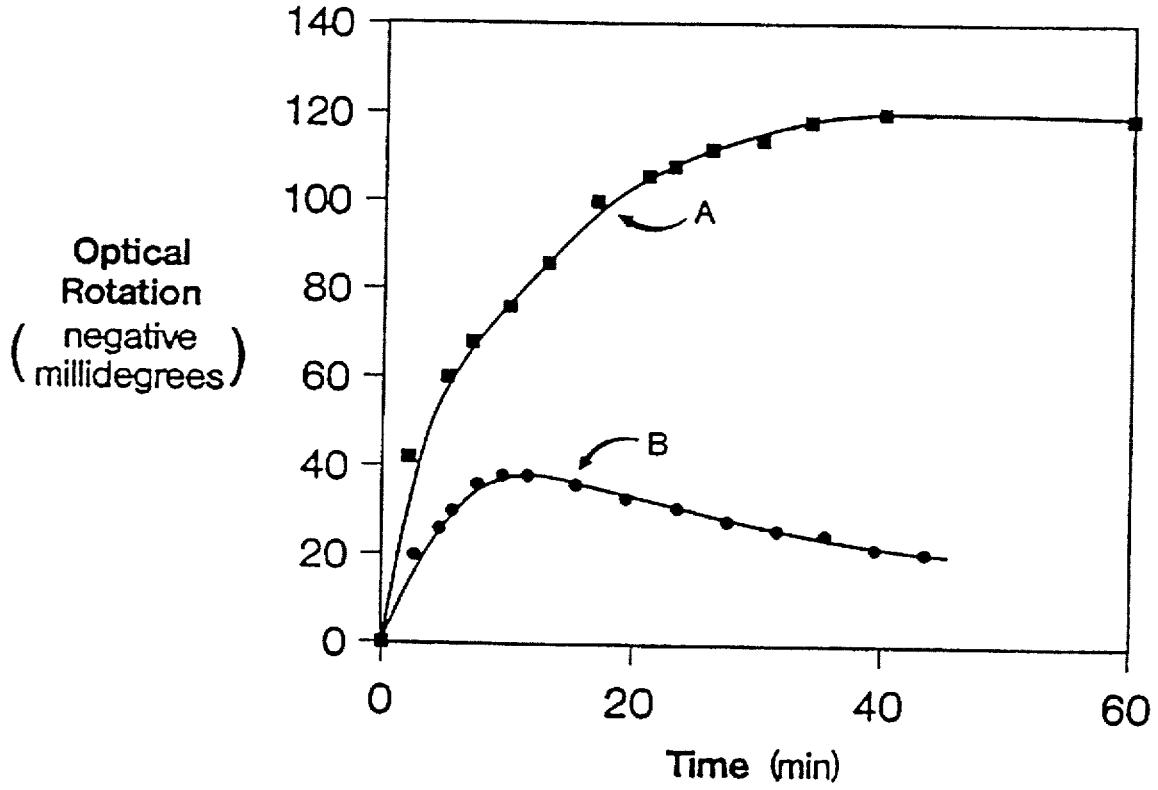
FIGS. 3–5 are a graphs showing the effectiveness of the process of the present invention.

Two 60 mM solutions of racemic benzaldehyde cyanohydrin in pH 5.5 citrate buffer were incubated at 25° C. with the enzyme (R)-oxynitrilase present in a concentration of 2.1 units/ml, and the optical rotation of the solutions were measured over approximately 45 minutes. One of the solutions, designated as solution A, was treated with the supported-gas membrane system of substantially the same type shown and discussed above in connection with FIG. 1, for the removal and trapping of the dehydrocyanation products HCN and benzaldehyde. The other solution, designated as solution B, had no dehydrocyanation product removed, and was simply allowed to approach thermodynamic equilibrium. The optical rotation of the solutions in both cases was negative due to the enantiomerically selective depletion of (R)-benzaldehyde cyanohydrin. In the case of solution B, the optical rotation leveled off and began to decrease over time as a result of racemization due to the back-reaction (or hydrocyanation reaction) of the dehydrocyanation products HCN and benzaldehyde. The results are shown in the plot comprising FIG. 3. As is apparent, the optical rotation of solution A leveled off at a much higher value than that of solution B, suggesting more extensive cleavage of (R)-benzaldehyde cyanohydrin. As is also apparent from FIG. 3, the optical rotation of solution A did not decrease over time, strongly suggesting that back-reaction of the dehydrocyanation products was insignificant because the concentrations of dehydrocyanation products was very low due to removal and trapping of the same.

EXAMPLE 2

Figure 4:
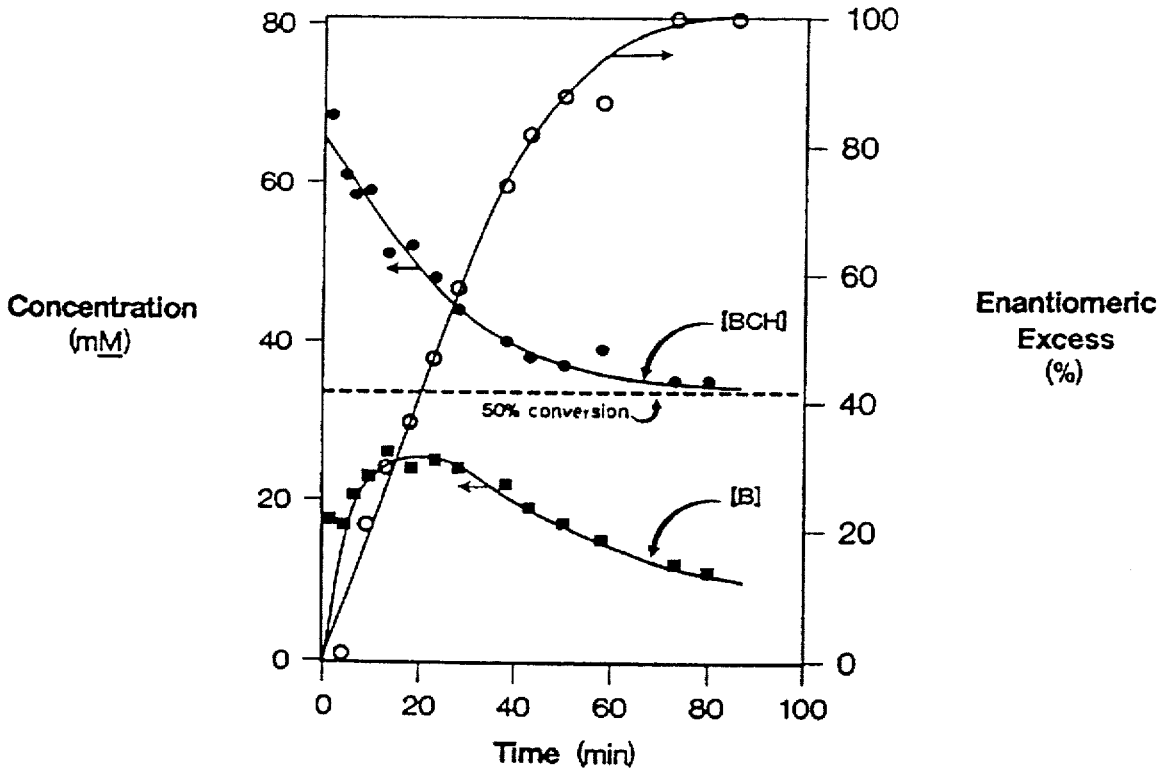

Example 1 was repeated with removal and trapping of the dehydrocyanation products in the same manner as was done for Solution A in that Example, and the solution was monitored for enantiomeric enrichment by optical rotation and for the total amount of benzaldehyde cyanohydrin and benzaldehyde by High Pressure Liquid Chromatography (HPLC). Based on measured concentrations of these moieties and the optical rotation, the enantiomeric excess of (S)-enantiomer was calculated over the course of the reaction (approximately 90 minutes in duration). The results are shown in the plot comprising FIG. 4. As is apparent, the total concentration of benzaldehyde cyanohydrin [BCH] leveled off at approximately half its starting value, consistent with selective dehydrocyanation of (R)-benzaldehyde cyanohydrin. Also consistent with such enantioselective dehydrocyanation was the observation that the enantiomeric excess of the desired enantiomer (S)-benzaldehyde cyanohydrin approached 100%. The results also showed that the concentration of benzaldehyde [B] rose during the early part of the reaction, but fell in the latter stages as it was removed and trapped via the supported-gas membrane.

EXAMPLE 3

Example 1 was substantially repeated, with the exceptions noted. The aqueous feed reservoir of the supported-gas membrane loop was charged with 500 ml of pH 5.5 citrate buffer, 5.32 grams of racemic benzaldehyde cyanohydrin (40 mmol), and sufficient (R)-oxynitrilase to obtain an activity of 7.4 units/mi. The strip reservoir was charged with 2 L of 0.5M aqueous sodium hydroxide. The feed reservoir and strip reservoir solutions were recirculated by peristaltic pumps at a flow rate of approximately 350 ml/min. Reaction progress was monitored by measuring optical rotation of the feed reservoir, which became progressively negative with time and approached a fixed value of –0.19°. After 80 minutes, contents of the feed reservoir were collected, the reaction quenched by the addition of concentrated sulfuric acid, and the product was isolated by extracting the mixture with two successive portions of chloroform (100 ml and 50 ml). The organic extracts were combined and dried over sodium sulfate. The organic extract had an optical rotation of –0.399°. HPLC analysis using a C-18 reverse phase column employing isocratic elution using methanol (0.05M aqueous trifluoroacetic acid) (60/40 vol/vol) with detection at 250 nm showed that the concentration of (S)-benzaldehyde cyanohydrin was 7.6± 0.4 g/ml. On the basis of the rotation at that concentration, the measured specific rotation of (S)-benzaldehyde cyanohydrin was –52.5°±–2.8°. Given the literature value for (R)-enantiomer of +49°, this was estimated to correspond to an enantiomeric excess (S)-enantiomer of approximately 100%.

EXAMPLES 4–8

Example 3 was substantially repeated, varying the cyanohydrin starting material, with the results noted in Table 3.

TABLE 3

| Example No. | Cyanohydrin | Reaction Time (hr) | Conversion (%) | Specific Rotation of Cyanohydrin (degrees) Measured | Literature* | ee % |
|---|---|---|---|---|---|---|
| 4 | p-Anisaidehyde cyanohydrin | 2 | 50 | −47.6 | +48 | 99 |
| 5 | Piperonal cyanohydrin | 2 | 50 | −46.3 | +47 | 99 |
| 6 | 5-Methylfurfural cyanohydrin | 106.5 | 61 | −38 | +79 | 48 |
| 7 | m-Anisaldehyde cyanohydrin | 3 | 66 | −30.9 | +36.6 | 84 |
| 8 | Furfural cyanohydrin | 2 | 63 | −44.4 | +51 | 87 |

*Highest specific rotation cited in the literature for the (R)-enantiomer.

EXAMPLE 9

Trapping by liquid-liquid extraction during dehydrocyanation was demonstrated. Ten ml of racemic m-phenoxy benzaldehyde cyanohydrin was combined with 100 ml of aqueous 20 mM citrate buffer (pH 5.5) containing 4000 units of (R)-oxynitrilase. Because m-phenoxybenzaldehyde cyanohydrin and its dehydrocyanation product, m-phenoxybenzaldehyde, are immiscible with water, the mixture forms a two-phase reaction system comprising an enzyme-containing aqueous buffer phase and an unreacted-cyanohydrin-containing organic phase. In this case, the dehydrocyanation reaction took place in the aqueous phase and the unreacted (R)- and (S)-cyanohydrin itself acted as an organic extractant to remove and trap the dehydrocyanation product (R)-m-phenoxybenzaldehyde across the organic/aqueous interface. The two-phase mixture was maintained at ambient temperature and stirred for 48 hours, and the reaction progress was monitored by HPLC to 50% conversion. The desired enantiomeric product (S)-m-phenoxybenzaldehyde cyanohydrin was identified by NMR, isolated by extraction with diethyl ether, dried, freed of solvent and its optical rotation measured. The specific rotation in toluene was found to be −23.4°, corresponding to an enantiomeric excess of 96% of the (S)-enantiomer.

EXAMPLES 10–13

Example 9 was substantially repeated, varying the starting cyanohydrin and organic extractant, with the results noted in Table 4.

TABLE 4

| Example No. | Cyanohydrin | pH | Extractant | Reaction Time (hr) | Conversion (%) | Specific Rotation of Cyanohydrin (degrees) Measured | Literature* | Exantiomeric Excess (%) |
|---|---|---|---|---|---|---|---|---|
| 11 | Furfural cyanohydrin | 5.5 | cyanohydrin | 48 | 39 | −29 | +51 | 57 |
| 12 | m-Anisaldehyde cyanohydrin | 5.5 | cyanohydrin | 72 | 41 | −24 | +36.6 | 65 |
| 13 | p-Anisaldehyde cyanohydrin | 5.5 | cyanohydrin | 48 | 48 | −27.4 | +48 | 57 |
| 14 | Piperonal cyanohydrin | 5.5 | cyanohydrin | 48 | 57 | −26.6 | +47 | 57 |
| 15 | m-Phenoxybenzaldehyde cyanohydrin | 5.5 | cyanohydrin | 48 | 54 | −16.2 | −24 | 67 |
| 16 | m-Phenoxybenzaldehyde cyanohydrin | 5.25 | cyanohydrin | 48 | 53 | −17.2 | −24 | 72 |
| 17 | m-Phenoxybenzaldehyde cyanohydrin | 5.0 | cyanohydrin | 48 | 51 | −19.2 | −24 | 81 |
| 18 | p-Anisaldehyde cyanohydrin | 4.5 | cyanohydrin | 48 | 51 | −36.2 | +48 | 75 |
| 19 | Piperonal cyanohydrin | 4.5 | cyanohydrin | 48 | 58 | −48 | +47 | 100 |

*Positive rotations correspond to highest specific rotation cited in the literature for the (R)-enantiomer.

EXAMPLES 14–16

The following examples demonstrate the need for pH control during dehydrocyanation. Example 9 was substantially repeated, except for a lower enzyme concentration and varying the pH of the aqueous citrate buffer. The results, summarized in Table 4, shows that although a decrease in pH decreases the rate of dehydrocyanation, evidenced by a decrease in the extent of conversion, there is a measurable improvement in the apparent selectivity, evidenced from the enantiomeric excess of the cyanohydrin remaining at the end of the reaction.

EXAMPLES 17–18

Examples 12 and 13 were substantially repeated, with exception that the pH of the aqueous citrate buffer was lowered from 5.5 to 4.5. The results, summarized in Table 4, show the expected improvement in enantiomeric excess.

EXAMPLES 19–24

The following procedures exemplify trapping by chemical reaction during dehydrocyanation with a soluble enantioselective catalyst to effect enantiomeric enrichment. Example 9 was substantially repeated, varying the cyanohydrin starting material and either including or keeping out one molar equivalent of cyclohexanone, which chemically trapped the hydrogen cyanide produced in the dehydrocyanation reaction. The results, summarized in Table 5, show that including cyclohexanone increases the extent of conversion and improves the enantiomeric excess of the cyanohydrin remaining at the end of the reaction.

TABLE 5

| Example No. | Cyanohydrin | Chemical Trapping pH | Reagent | Reaction Time (hr) | Conversion (%) | Specific Rotation of Cyanohydrin (degrees) Measured | Literature* | Exantiomeric Excess (%) |
|---|---|---|---|---|---|---|---|---|
| 20 | Benzaldehyde cyanohydrin | 5.5 | none | 48 | 25 | −0.40 | −49.0 | 1 |
| 21 | Benzaldehyde cyanohydrin | 5.5 | cyclohexanone | 48 | 36 | −8.26 | −49.0 | 24 |
| 22 | 5-Methylfurfural cyanohydrin | 5.5 | none | 48 | 44 | −21.7 | −79 | 27 |
| 23 | 5-Methylfurfural cyanohydrin | 5.5 | cyclohexanone | 48 | 61 | −38 | −79 | 48 |
| 24 | Piperonal cyanohydrin | 5.5 | none | 48 | 57 | −26.6 | −47 | 57 |
| 25 | Piperonal cyanohydrin | 5.5 | cyclohexanone | 48 | 76 | −41.6 | −47 | 89 |

*Positive rotations correspond to highest specific rotation cited in the literature for the (R)-enantiomer.

EXAMPLE 25

The following procedure exemplifies use of a combination of trapping methods (gas-liquid extraction and liquid-liquid extraction) during dehydrocyanation to effect enantiomeric enrichment.

A 100 ml three-necked flask was charged with 5 ml of racemic m-phenoxybenzaldehyde cyanohydrin and 50 ml of aqueous 20 mM citrate buffer (pH 5.5) containing 2000 units of (R)-oxynitrilase. The contents of the flask were stirred with a magnetic stirrer and sparged continuously with a flow of nitrogen to remove hydrogen cyanide produced in the dehydrocyanation. To prevent the loss of water in the reaction mixture through evaporation, nitrogen gas was presaturated with water by bubbling through a water trap. The two-phase mixture was maintained at ambient temperature and the reaction progress was monitored by gas chromatography. After 24 hours, the reaction had progressed to 43% conversion and the enantiomeric excess of m-phenoxybenzaldehyde cyanohydrin remaining was 81% of the (S)-enantiomer.

EXAMPLE 26

The following procedure exemplifies the use of another combination of trapping methods (supported-gas membrane and membrane-based liquid-liquid extraction) during dehydrocyanation to effect enantiomeric enrichment. A combination membrane contactor/supported-gas membrane of the type shown in and discussed above in connection with FIG. 2 was used to remove and trap the dehydrocyanation cleavage reaction products. The organic feed reservoir was charged with a solution of 20 grams of racemic benzaldehyde cyanohydrin in 140 ml of toluene/heptane (80/20; vol/vol); the aqueous enzyme reservoir was charged with 500 ml of aqueous 0.1M sodium citrate buffer (pH 5.5) containing 6 units/ml of (R)-oxynitrilase; and the aqueous strip reservoir was charged with 3 L of 0.17M aqueous sodium hydroxide. The temperature of the reservoirs was maintained at about 4° C. and peristaltic pumps were used to circulate the solutions at approximately 150 ml/min.

Figure 5:
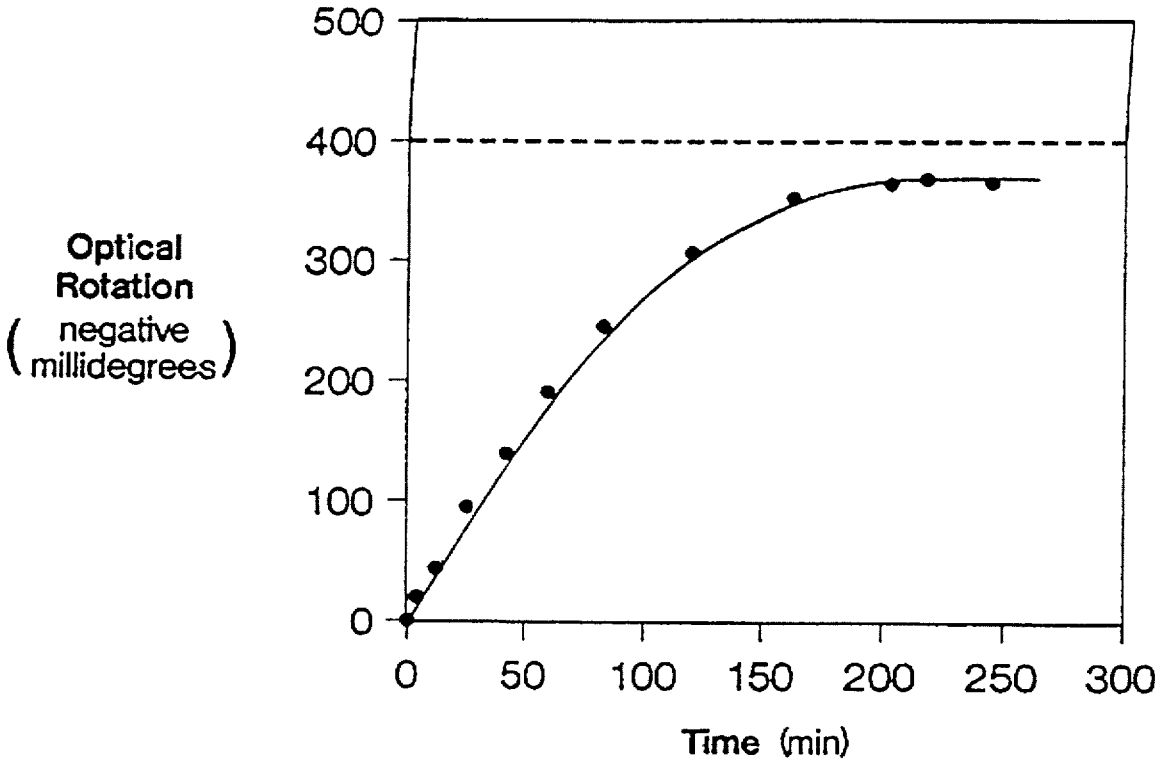

At various times, aliquots were removed from the organic feed and aqueous enzyme reservoirs, and the optical rotations of the samples were measured. The results from the aqueous enzyme are shown in the plot comprising FIG. 5 where the dashed horizontal line comprises the calculated optical rotation of the solution that corresponds to 100% enantiomeric excess of (S)-cyanohydrin. As is apparent, after approximately three hours the optical rotation of (S)-benzaldehyde cyanohydrin leveled off at a value approaching 100% enantiomeric excess (actual measured was 92%). (S)-benzaldehyde cyanohydrin in the organic reservoir was isolated and its optical rotation measured, which was found to corresponded to an 82% enantiomeric excess. Overall yield of the (S)-cyanohydrin enantiomer was 82%.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. An enzymatic process for the enantiomeric enrichment of a chiral cyanohydrin of the structure

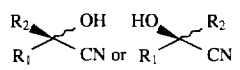

comprising the steps:

(a) bringing said mixture of chiral cyanohydrins into contact at a pH of 3.5 to 5.5 with an enantioselective dehydrocyanation catalyst selected from the group consisting of (R)- and (S)- oxynitrilase and cyclic peptides until one of said chiral cyanohydrins is converted in a dehydrocyanation reaction to dehydrocyanation reaction products comprising hydrogen cyanide and an aldehyde or ketone of the structure

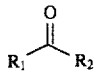

(b) simultaneously reducing the concentration of at least one of said dehydrocyanation reaction products by a method selected from a liquid-liquid extraction, a liquid-gas extraction, a membrane-based separation, a chemical conversion, and combinations thereof where
(i) $R_1$ and $R_2$, taken together, form a diyl hydrocarbon chain containing 3 to 5 carbons, or
(ii) $R_1$ and $R_2$ are different and $R_1$ is selected from straight and branched chain alkyl, cycloalkyl, heterocyclic and aryl groups, said cycloalkyl, said heterocyclic and said aryl groups being unsubstituted or substituted with a substituent selected from the groups consisting of halo, hydroxy, lower alkyl, lower alkoxy, lower alkylthio, cycloalkyl, carbamoyl, trifluoromethyl, phenyl, *phenoxy,* nitro, alkylsulfonyl, arylsulfonyl, alkylcarboxamide, and [acrylcarboxamido,] *arylcarboxamido,* and $R_2$ is selected from hydrogen and $R_1$.

2. The process of claim 1 wherein step (a) is conducted in a liquid phase selected from an organic, an aqueous, an organic/organic mixture, and an organic/aqueous mixture.

3. The process of claim 1 wherein step (b) is conducted by a liquid-liquid extraction and the liquid in said extraction is an organic liquid.

4. The process of claim 3 wherein said organic liquid in said extraction is a cyanohydrin.

5. The method of claim 1 wherein step (b) is conducted by a liquid-liquid extraction and the liquid in said extraction is a mixture of immiscible liquids.

6. The method of claim 1 wherein step (b) is conducted by a liquid-gas extraction utilizing gas as a sweep or a sparge.

7. The method of claim 1 wherein step (b) is conducted by a membrane-based separation selected from a method utilizing a supported-gas membrane or a membrane contactor.

8. The method of claim 7 wherein step (b) is conducted by a method utilizing a hydrophilic supported-gas membrane.

9. The method of claim 7 wherein step (b) is conducted by a method utilizing a hydrophobic supported-gas membrane.

10. The method of claim 9 wherein a polymer is coated on said hydrophobic supported-gas membrane.

11. The method of claim 10 wherein said polymer is poly(dimethylsiloxane).

12. The method of claim 1 wherein step (b) is conducted by a chemical conversion of the dehydrocyanation *reaction* product hydrogen cyanide to form a cyanohydrin, said chemical conversion being selected from hydrolysis, alkylation and hydrocyanation.

13. The method of claim 1 wherein step (b) is conducted by a chemical conversion of the dehydrocyanation reaction product aldehyde or ketone that is selected from reactions with compounds selected from the group consisting of bisulfites, amines, diamines, hydroxylamines, hydrazines, and oxidants.

14. The method of claim 1 wherein said dehydrocyanation catalyst of step (a) is dissolved or immobilized.

15. The method of claim 1 wherein $R_1$ is m-phenoxyphenyl, $R_2$ is hydrogen and said dehydrocyanation catalyst of step (a) is (R)-oxynitrilase.

16. The method of claim 1 wherein $R_2$ is hydrogen and $R_1$ is selected from m- and p-methoxyphenyl; furfuryl and 5-methylfurfuryl; and piperonyl.

17. The method of claim 1 wherein step (b) is conducted by contacting said cyanohydrin dehydrocyanation products with one side of a two-sided supported-gas membrane and circulating an aqueous alkaline solution on the other side of said supported-gas membrane.

18. The method of claim 1 wherein step (b) is conducted by extraction of said aldehyde or ketone cleavage product into an organic liquid.

19. The method of claim 1 wherein step (b) is conducted by a membrane-based separation utilizing a combination of a supported-gas membrane and a membrane contactor.

* * * * *